(12) United States Patent
Hunt et al.

(10) Patent No.: US 7,254,211 B2
(45) Date of Patent: Aug. 7, 2007

(54) METHOD AND APPARATUS FOR PERFORMING COMPUTED TOMOGRAPHY

(75) Inventors: Frank Hunt, West Bloomfield, MI (US); Kaname Sasaki, Farmington Hills, MI (US); Shigeru Oho, Farmington Hills, MI (US)

(73) Assignee: Hitachi, Ltd., Tokyo (JP)

( * ) Notice: Subject to any disclaimer, the term of this patent is extended or adjusted under 35 U.S.C. 154(b) by 59 days.

(21) Appl. No.: 10/940,924

(22) Filed: Sep. 14, 2004

(65) Prior Publication Data

US 2006/0056577 A1    Mar. 16, 2006

(51) Int. Cl.
*G01N 23/00* (2006.01)

(52) U.S. Cl. .......................................... 378/20; 378/57

(58) Field of Classification Search .................. 378/57, 378/79, 4–20, 195–196, 208, 197–198, 177, 378/58, 55, 21, 62, 205
See application file for complete search history.

(56) References Cited

U.S. PATENT DOCUMENTS

| | | | | |
|---|---|---|---|---|
| 3,766,387 | A | | 10/1973 | Heffan et al. ............... 250/83.3 |
| 4,718,010 | A | | 1/1988 | Fujii .......................... 364/414 |
| 4,803,639 | A | | 2/1989 | Steele et al. ................. 364/507 |
| 4,989,225 | A | * | 1/1991 | Gupta et al. .................... 378/10 |
| 5,023,895 | A | | 6/1991 | McCroskey et al. ........... 378/4 |
| 6,327,328 | B1 | * | 12/2001 | Satoh et al. .................... 378/17 |
| 6,334,708 | B1 | * | 1/2002 | Kosugi ........................ 378/197 |
| 6,501,826 | B1 | * | 12/2002 | Kropfeld ................. 378/98.12 |
| 6,628,981 | B2 | * | 9/2003 | Baker et al. ................. 600/425 |
| 6,785,357 | B2 | * | 8/2004 | Bernardi et al. ............... 378/57 |
| 2003/0021381 | A1 | * | 1/2003 | Koppe et al. ................ 378/163 |
| 2003/0031300 | A1 | * | 2/2003 | Cheng ......................... 378/177 |
| 2003/0128869 | A1 | | 7/2003 | Grass et al. ................. 382/131 |
| 2003/0147489 | A1 | | 8/2003 | Bijjani et al. ................... 378/4 |
| 2004/0109532 | A1 | * | 6/2004 | Ford et al. ..................... 378/57 |

FOREIGN PATENT DOCUMENTS

| | | | |
|---|---|---|---|
| JP | 60036942 | | 2/1985 |
| JP | 362067432 A | * | 3/1987 |
| JP | 2093350 | | 4/1990 |
| JP | 402206789 A | * | 8/1990 |
| JP | 3179242 | | 8/1991 |

\* cited by examiner

*Primary Examiner*—Hoon Song
(74) *Attorney, Agent, or Firm*—Gifford, Krass, Sprinkle, Anderson & Citkowski, P.C.

(57) ABSTRACT

An apparatus for performing computed tomography having a radiation source and at least one radiation detector spaced from the radiation source and which generates an output signal representative of the strength of the received radiation from the radiation source. A part support for holding a plurality of parts is positioned in between the radiation source and the detectors. The part support is rotatably mounted about an axis generally perpendicular to a vector between the radiation source and the detectors so that, upon rotation of the part support, the radiation detectors generate an output signal corresponding to the internal structure of parts supported on the part support. A computer system receives the output signals from the detectors and, under program control, generates a report of the internal structure of the parts on the part support.

33 Claims, 7 Drawing Sheets

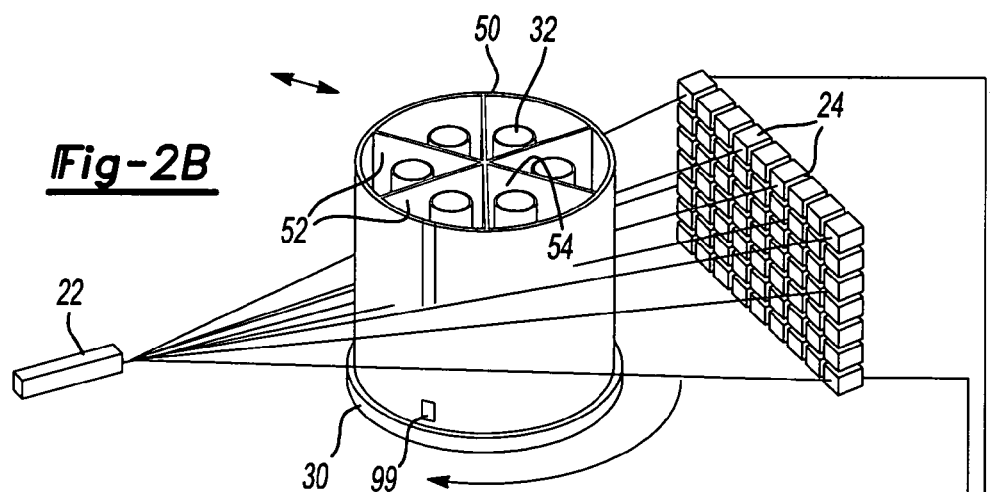
*Fig-2B*
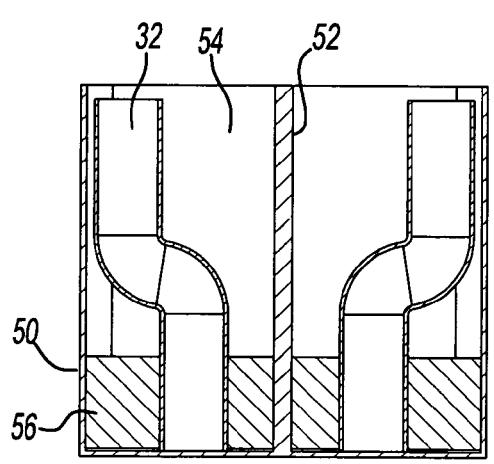
*Fig-3*
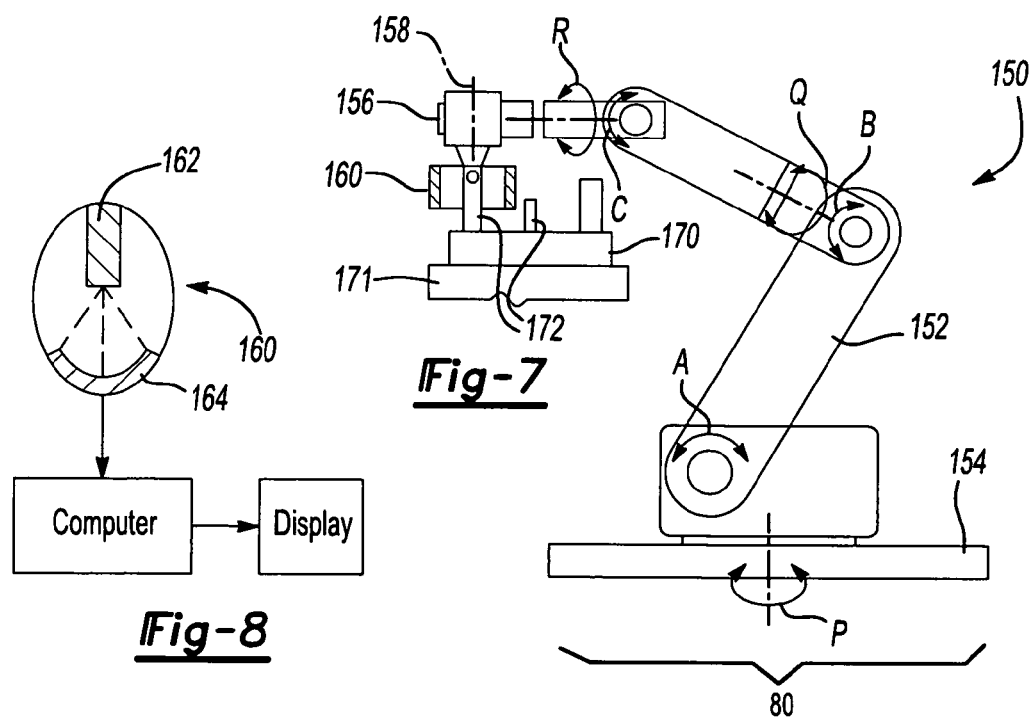
*Fig-7*
*Fig-8*

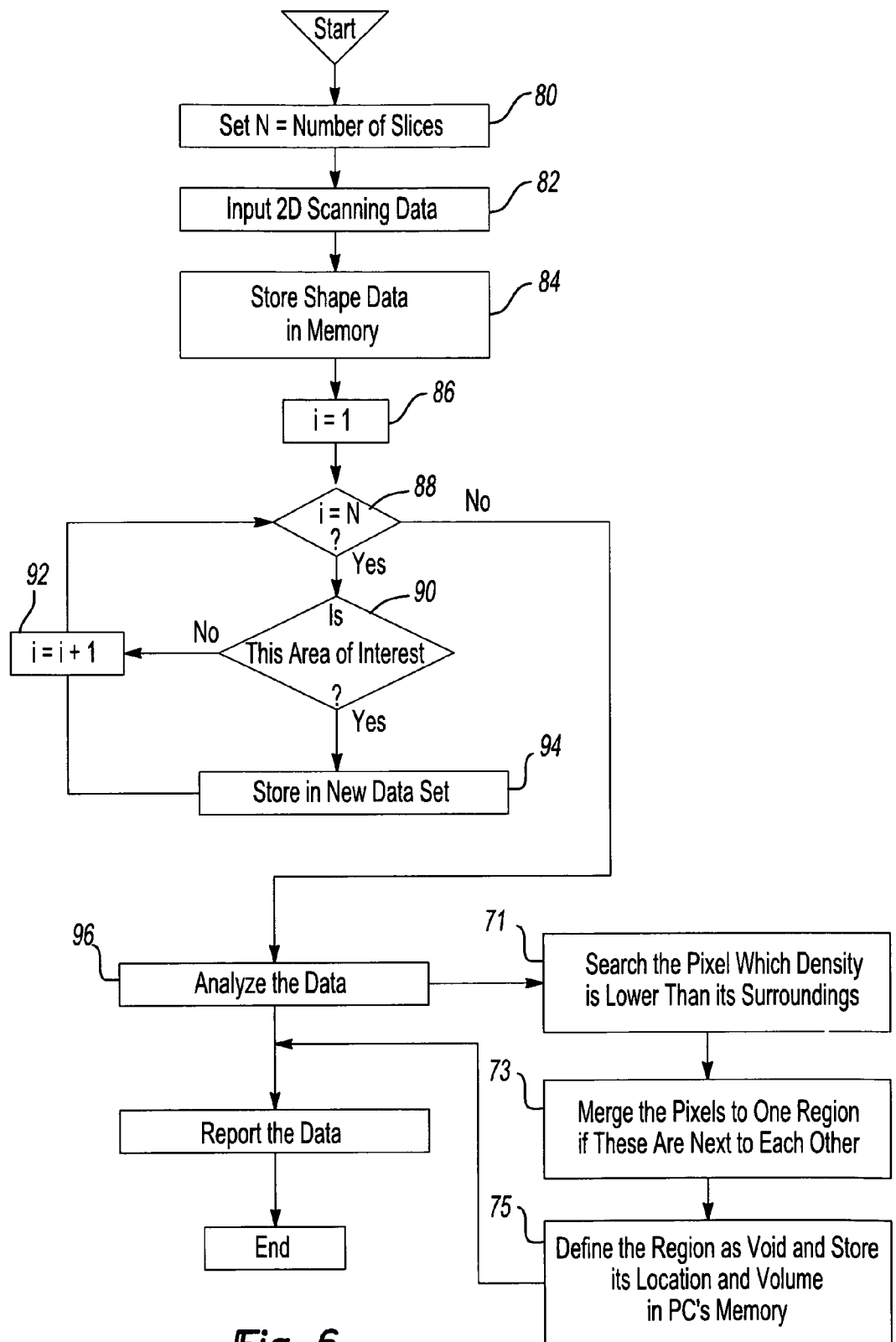

METHOD AND APPARATUS FOR PERFORMING COMPUTED TOMOGRAPHY

BACKGROUND OF THE INVENTION

I. Field of the Invention

The present invention relates generally to an apparatus and method for performing computed tomography.

II. Description of Related Art

There are many situations where it is highly desirable to examine a component to determine if the internal structure of the component contains voids or other flawsas well as dimensional accuracy. In the automotive industry there are many components which, if these components contain a void or other flaw, would compromise the overall operation of the vehicle. For example, a void or other flaw in the engine block closely adjacent the combustion chamber may cause a complete failure of the engine during operation or otherwise compromise the safety and/or performance of the engine.

Such internal flaws of parts are not visible from the exterior of the part. In the automotive industry, internal portions of automotive parts have previously been visually inspected by destructive testing, where the part is physically cut into pieces. The destructive testing process has the disadvantage of destroying the sample, causing new defects during the cutting process and not allowing a large sample or all of the pieces to be inspected. Consequently, in order to examine these parts, there are previously known computed tomography (CT) machines. Such CT machines typically include an x-ray source and one or more x-ray detectors or x-ray film at a position spaced from the source. Each x-ray detector generates an output signal which varies in magnitude with the strength of the received signal from the radiation source.

The part to be examined is then positioned in between the radiation source and the radiation detector or detectors. The part is then scanned by rotating the part relative to the radiation source and the radiation detector thus performing a two-dimensional (2D) x-ray image of the part representative of the density of the part. Successive 2D imaging of the part at axially spaced positions along the part produces individual 2D slices which, when combined, produce a three-dimensional image of the interior structure of the part. In practice, a void within the interior of the part will create an increase in the detected radiation by the detector during the 2D imaging since voids necessarily absorb less radiation than the homogenous structure of the part.

The output from the detectors is then connected to a computer system which then generates an image of the internal structure of the part under examination. Any voids or other defects within the interior of the part are visible on the reconstructed image.

These previously known CT machines, however, all suffer from a number of common disadvantages. One disadvantage of the CT machine is that previously it has only been possible to scan a single part or component at a given time. Furthermore, a complete scan of the part takes an extended period of time which varies as a function of the number of 2D images performed.

Since a complete CT scan of a single part is time consuming, it is not practical to scan all of the production parts in a high part volume situation. Consequently, it has been the previous practice to simply select sample parts from the production run and to examine these parts using a CT machine. However, unexamined parts may contain serious voids or other flaws and yet go undetected.

A still further disadvantage of the previously known method for scanning individual parts with a CT machine is that the parts to be examined are typically shipped from the production facility and to the CT machine facility. At the CT machine facility, the parts are removed from their packaging and mounted on a fixture between the radiation source and detector of the CT machine. Following a complete scan of the part, the part is removed from the CT machine, reinserted into the shipping carton from the production facility, and shipped back to the production facility. All of these procedures, however, are necessarily labor intensive and thus expensive in labor cost.

SUMMARY OF THE PRESENT INVENTION

The present invention provides both a method and apparatus for CT scanning which overcomes all of the above-mentioned disadvantages of the previously known devices.

In brief, the device of the present invention comprises a radiation source, typically an x-ray source, and at least one radiation detector spaced from the radiation source. This radiation detector generates an output signal representative of the strength of the received radiation from the radiation source.

A part support for supporting a plurality of parts is then positioned in between the radiation source and the radiation detectors. Preferably, the part support is positioned on a rotatable table which rotates about an axis generally perpendicular to a vector between the radiation source and the radiation detector.

During a CT scan, all of the parts supported on the part support are simultaneously scanned by the radiation source and radiation detectors. During the simultaneous scan, the output signals from the radiation detectors each generate an output signal representative of the strength of the received radiation from the radiation source. In the conventional fashion a 2D image is performed per revolution of the parts and successive scanning of axially displaced positions produces a three-dimensional scan of the parts.

The outputs from the radiation detectors are connected to a computer system as input signals. The computer system, under program control, recombines the 2D image slices and then generates a three-dimensional report or image of the internal structure of all of the parts mounted on the part support.

Preferably, the parts are contained within a shipping container. The parts may be positioned either in a symmetrical or asymmetrical orientation within the shipping container. However, during the CT scan operation, the entire container with its contained parts is simultaneously scanned thus eliminating the previously known necessity of removing the individual parts from their shipping containers. Additionally, the scanning data representing any partitions in the container are disregarded thereby reducing the time necessary to process the data.

In many instances a flaw or void in only a portion of the part is critical to the acceptability of the part. For example a void closely adjacent the combustion chamber of an engine block would render the part unacceptable while a void in other portions of the block would be acceptable. Thus, as a further aspect of the present invention only the data for the critical portions of the part are processed by the computer. This results in reduced computer processing times.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 2B is a view similar to FIG. 2A, but illustratively modification thereof;

FIG. 3 is a sectional view illustrating an exemplary container for the parts;

FIG. 6 is a flowchart illustrating a second preferred embodiment of the present invention;

FIG. 7 is a side diagrammatic view illustrating still a further preferred embodiment of the present invention;

FIG. 8 is a plan diagrammatic view illustrating a portion of the preferred embodiment of the invention shown in FIG. 7;

DETAILED DESCRIPTION OF A PREFERRED EMBODIMENT OF THE PRESENT INVENTION

Figure 1:
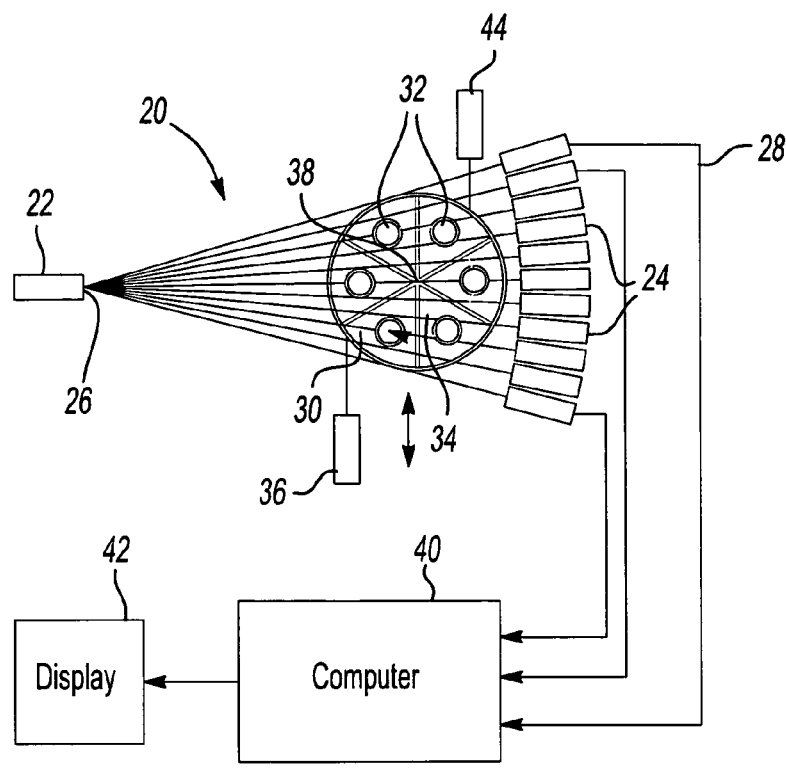
FIG. 1 is a top plan diagrammatical view illustrating a first preferred embodiment of the present invention.
Figure 2A:
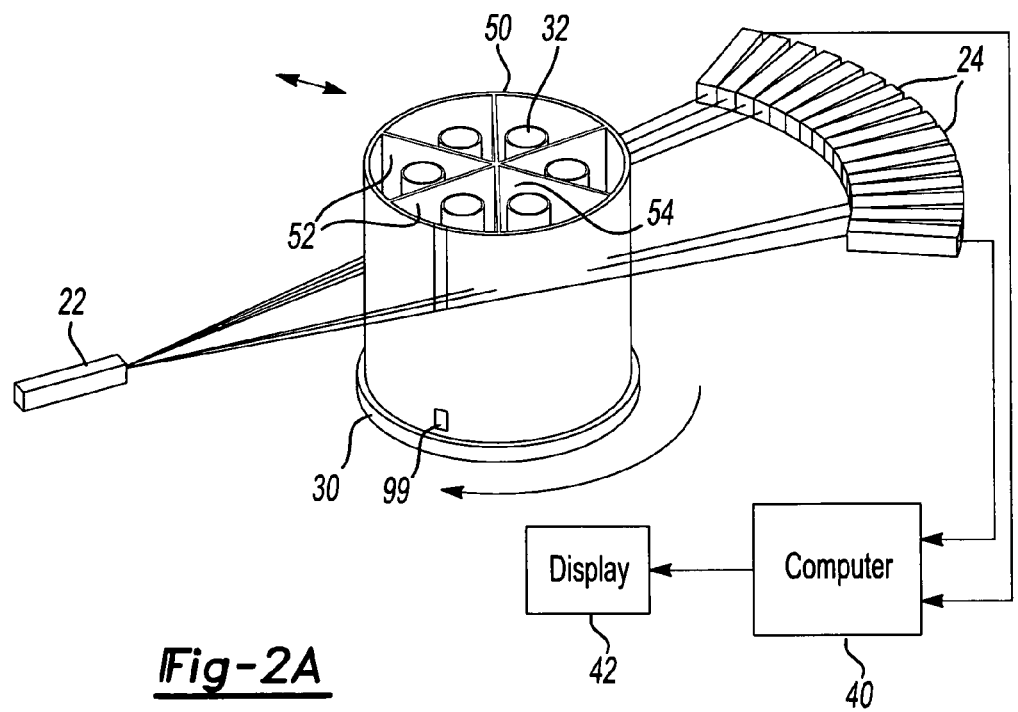
FIG. 2A is an elevational diagrammatic view illustrating a second preferred embodiment of the present invention.

With reference first to FIGS. 1 and 2A, a diagrammatic view of a preferred embodiment of a CT scanning system 20 is shown and includes a radiation source 22. The radiation source 22 is preferably an x-ray radiation source and may be of any conventional construction.

A plurality of radiation detectors 24 are arranged at a position spaced from the radiation source 22. The radiation detectors 24 are linearly positioned side by side to each other and are preferably arranged in an arc having a center at the output 26 of the radiation source 22. Each radiation detector 24, furthermore, generates an output signal on its output 28 which varies proportionately with the strength of the received radiation from the radiation source 22. The radiation detectors 24 may be of any conventional construction and typically provide an analog output signal on their individual outputs 28 within a predetermined voltage range.

With reference to FIG. 2B, the radiation detectors 24 may alternatively be arranged in a two-dimensional array 25. In this event, the radiation source 22 provides a generally conical output such that radiation from the source 22 is simultaneously received by all of the detectors 24 in the array 25.

Still referring to FIG. 1, a part support 30, preferably a rotary table, is positioned in between the radiation source 22 and the radiation detectors 24. A plurality of parts 32 are positioned on and supported by the part support 30. Preferably, the parts 32 are positioned around the outer periphery of the part support 30 and thus radially spaced from the center 34 of the part support 30.

An actuator 36 (illustrated only diagrammatically), such as a motor, rotates the part support 30 about its axis 38 generally perpendicular to a vector between the radiation source 22 and the detectors 24 and, in doing so, rotates the parts 32 through the radiation from the radiation source 22. During the rotation of the part support 30, the parts 32 absorb a portion of the radiation from the radiation source 26. Consequently, the output signal from the radiation detectors 24 on their individual outputs 28 will likewise vary in accordance with the absorption of the radiation by the parts 32. Any voids contained within the parts 32, however, will absorb less radiation than a homogenous structure for the interior structure of the parts and thus result in a higher output from the radiation detectors 24.

The outputs 28 from the radiation detectors 24 are coupled as input signals to a processor 40, such as a computer system. The processor 40 is programmed to analyze the data from the radiation detectors 24, i.e. the output signals from the radiation detectors 24 as a function of the rotational position of the part support 30. Following analysis of the data which will subsequently be described in greater detail, the processor 40 generates an output signal to a display device 42, such as a video screen, representative of an image of the internal structure of the parts 32 supported on the part support 30.

In practice, the CT scanning system 20 of the present invention performs a 2D image scan per revolution of the support 30 and thus generates an image corresponding to a single slice of the parts 32 supported on the part support 30. In order to scan the remainder of the parts 32, a second actuator 44 (illustrated only diagrammatically) is coupled with the part support 30 and axially shifts the part support 30 with its supported parts 32 a predetermined increment in the direction of the part support rotational axis 38 at the conclusion of each revolution of the part support 30. Consequently, in order to generate a three-dimensional image, the processor 40 combines the 2D images to form a three-dimensional image which is displayed on the display device 42.

In the event that an array 25 of radiation detectors 24 (FIG. 2B) is utilized and the array 25 is large enough to receive the radiation through all of the ports, it is unnecessary to axially shift the port support 30 to perform the entire CT scan. Conversely, if the array 25 is insufficiently large to receive scanning data for all of the ports during a simple rotation office port support 30, the port support 30 is axially displaced by an amount corresponding to the vertical height of the array 25 after each rotation of the port support 30.

In the CT scanning system 20 illustrated in FIG. 1, the parts 32 are simply supported on the part support 30. Preferably, the parts 32 are positioned at predefined positions on the part support 30 and this is accomplished by the appropriate fixture on the part support 30. Additionally, both the actuators 36 and 44 operate under control of the computer system 40 so that the processor 40 controls both the rotational position of the part support 30 as well as its axial position.

Figure 11A:
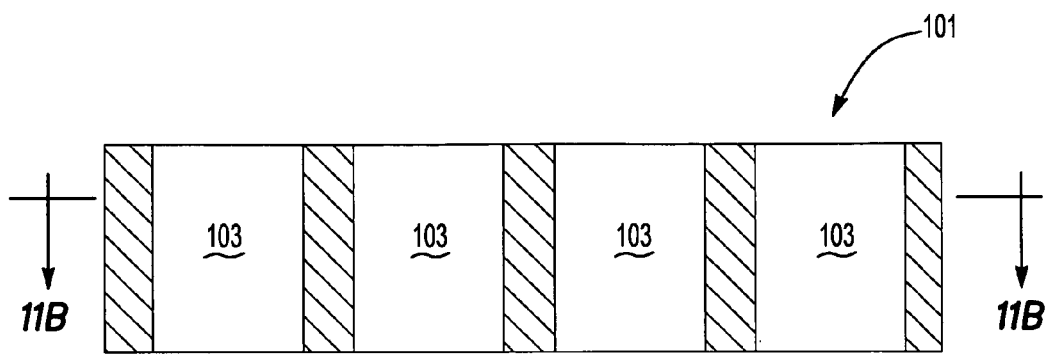
FIG. 11A is a side sectional view of a CT scan of an exemplary part.
Figure 11B:
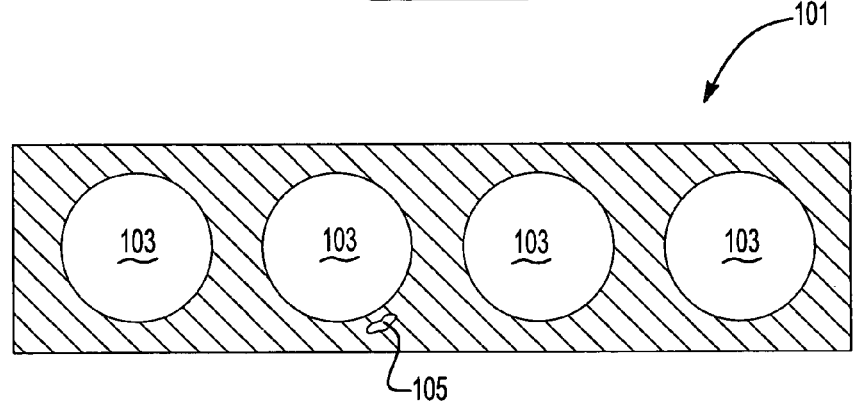
FIG. 11B is a sectional view taken along line 11B-11B in FIG. 11A.

An exemplary CT scan for a typical metal automotive part, an engine block 101 having four cylinders 103, is shown in FIGS. 11A and 11B. The voids or empty area are outputted by the system in the color white while the metal structure of the engine block is outputted as a shaded area. A void 105 in the engine block near one combustion chamber is also detected. Since the void 105 is near the cylinder wall, the engine block 101 would be rejected as a bad part.

With reference now to FIG. 2A, a modification of the CT apparatus 20 is illustrated in which the parts 32 are positioned within a container 50 and the container 50 is then mounted on the part support 30. The container 50 includes a plurality of partitions 52 which together form a plurality of compartments 54 with one part 32 being positioned within each compartment. The positioning of the parts 32 within their individual compartments 54 may be either symmetrical or asymmetrical. Furthermore, as shown in FIG. 3, each compartment 54 may include its own fixture 56, such as a molded base, to orient the part 32 in a predetermined orientation within its individual compartment 54.

In practice the container 50 also absorbs radiation from the radiation source 22. Therefore, data from the radiation detectors 24 corresponding to the container 50 and its partitions 52 should be disregarded. Furthermore, since the degree of radiation absorption of the container partitions is known, or at least can be determined, the data pertaining to the partitions may be identified.

Figure 9:
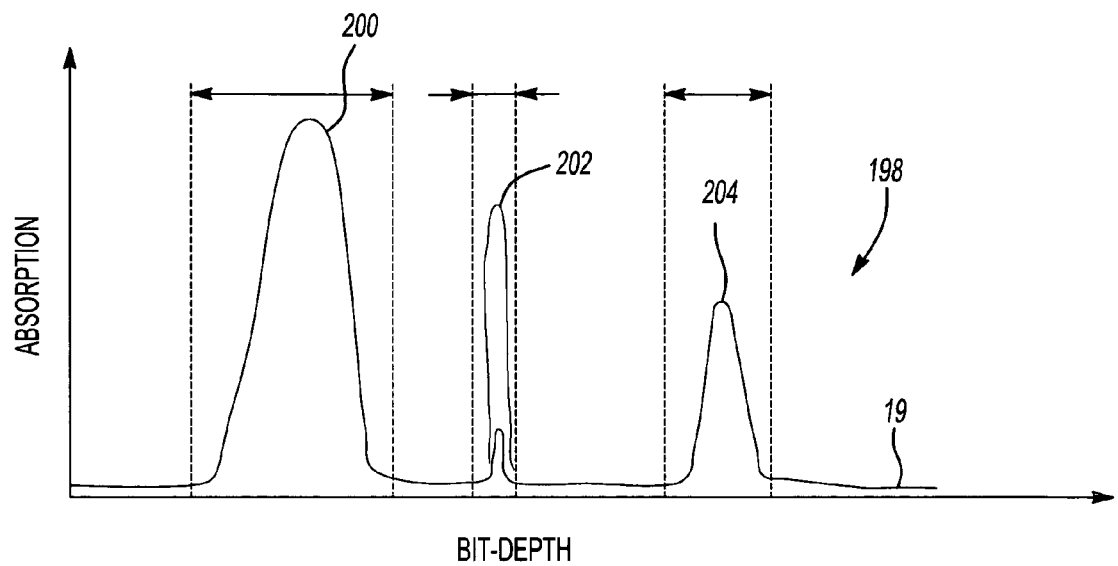
FIG. 9 is an exemplary graph of radiation absorption.

With reference to FIG. 9, an exemplary graph 198 showing the radiation absorption of parts in the container of FIG. 2 is shown. At peak 200 on the graph 198 a very low level of radiation absorption is shown corresponding to air or a void. A lower peak 202 corresponds to the partition 52. Since the partition 52 absorbs some radiation, a still lower peak 204, and thus greater radiation absorption, is indicative of the denser part. Consequently, the partition 52 is identified by the magnitude of the radiation received by the radiation detectors as differentiated from air and/or the denser part. The shape data corresponding to the container of FIG. 2 is shown in FIG. 11.

Figure 4:
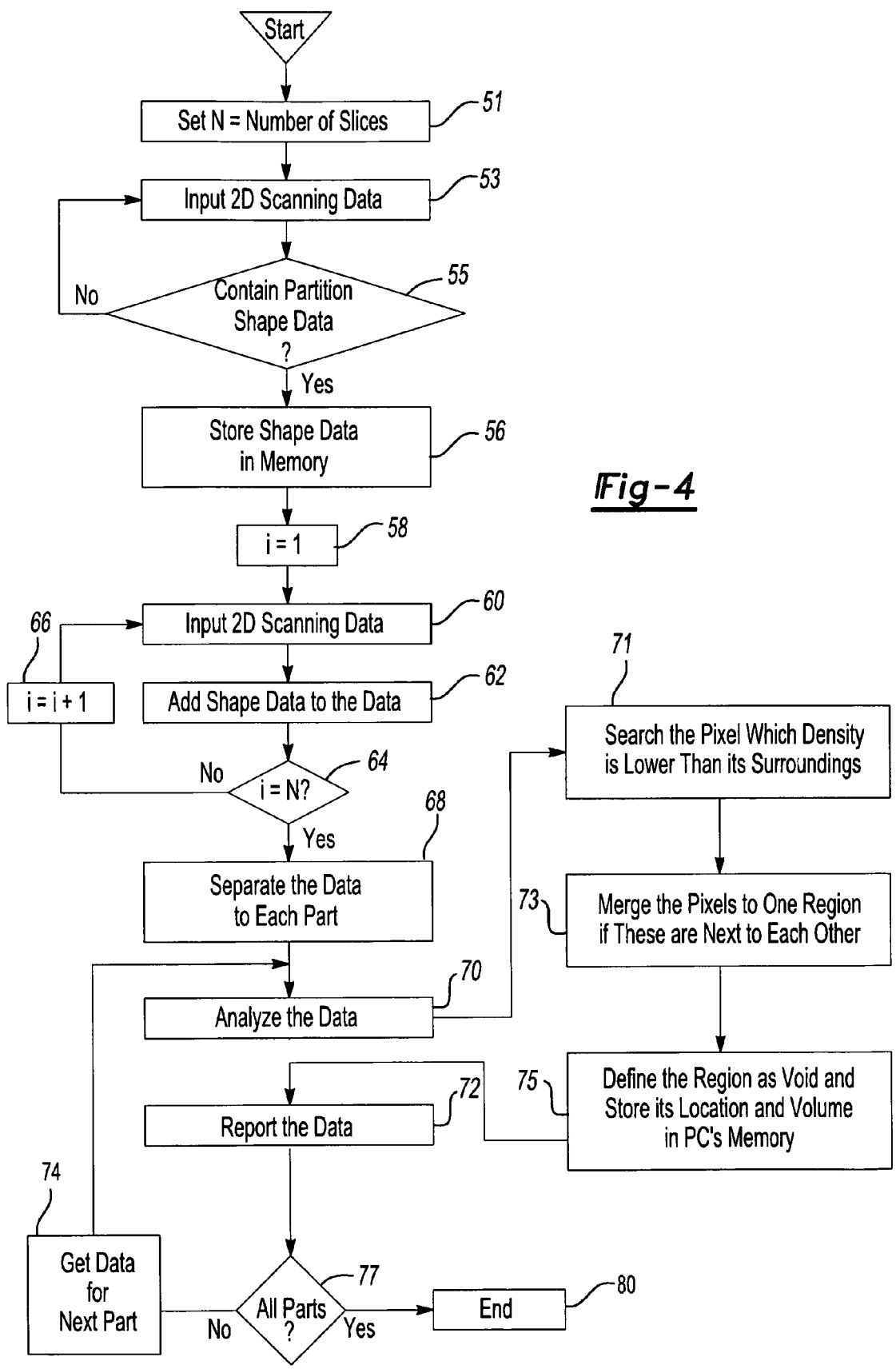
FIG. 4 is a flowchart illustrating the operation of one preferred embodiment of the invention.

With reference then to FIG. 4, a flowchart which processes the scanned data, including both parts and the container, and disregards the scanned data corresponding to the container partitions 52 is shown. After the parts and container have been completely scanned in N number of 2D slices and the combined data stored in memory, at step 51 the variable N is set to the number of vertical slices, i.e. the number of 2D scans, to be processed. Step 51 then proceeds to step 53 in which the data from the first 2D scan is recalled from memory. Step 53 then branches to step 55.

At step 55, the computer 40 determines whether or not the data from the first 2D slice contains data corresponding to the container partitions 52, e.g. as shown in FIG. 11. This determination is made by examination of the radiation absorption as per the graph of FIG. 10. If the data inputted at step 52 contains shape data corresponding to the partitions 52, step 55 proceeds to step 56. Otherwise, step 55 branches back to step 52 and examines the next 2D data slice until the shape data for the partitions 52 is found.

Figure 10:
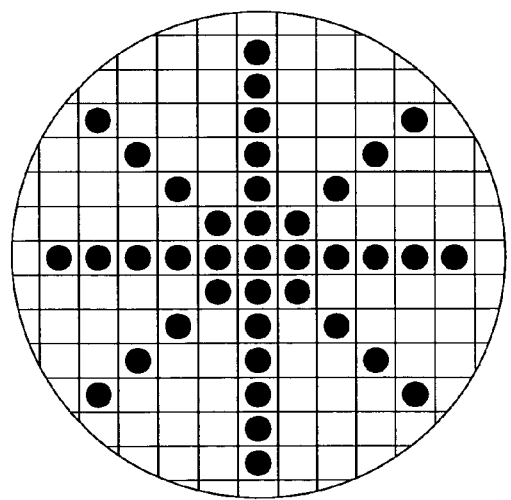
FIG. 10 is an exemplary shape data for a container.

At step 56 the shape data for the container partitions are stored in memory, e.g. the shape data shown in FIG. 10. Such memory may be computer random access and/or persistent memory, separate memory or memory accessible by a network. Step 56 then proceeds to step 58 where the variable i is set to 1 and step 58 then proceeds to step 60.

At step 60 the computer inputs the data for the $i^{th}$ 2D scan and then proceeds to step 62. At step 62 the shape data corresponding to the container partitions and previously stored at step 56 is added to the data for the $i^{th}$ 2D scan thus effectively eliminating the partition data from the data slices. Step 62 then proceeds to step 64 which determines if all of the scanned data slices as set by N in step 50 have been processed to eliminate the data corresponding to container partitions 52. If not, step 64 branches to step 66 which increments the variable i and the above procedure is repeated until each data slice has been processed to eliminate the container partition data.

When N finally equals i, i.e. all of the data slices have been processed to eliminate the container partitions 52, step 54 branches to step 68 where the data corresponding to each part within the container 50 are separated from the data corresponding to the other parts. For example, in the exemplary container illustrated in FIG. 2, the container 50 contains six parts. Consequently, at step 68 the data for each of the individual six parts is separated from the others prior to analyzing that data. Step 68 then proceeds to step 70 where the data corresponding to the first part is analyzed.

In order to analyze the data from the first part, step 70 branches to step 71 in which the computer under software control searches for pixels in which the density is lower than the surrounding pixels. Such a lower density is indicative of a void or flaw in the part. Step 71 then branches to step 73.

At step 73, the program merges the pixels identified at step 71 which are adjacent to each other. Such pixels may be adjacent not only in a single 2D slice but also in the adjacent 2D scan slices for the part. Step 73 then proceeds to step 75. At step 75 the computer then defines the regions merged at step 73 as a void in the part. Step 75 then stores the location and volume of that void in memory and then proceeds to step 72 where the information is outputted or reported, e.g. by displaying the results of the analysis on the display device 42 by a printed report, by a printed image, and/or the like. For example, voids in the part may be displayed, either on a video display or a printed image, in one color while homogenous portions of the part are displayed in a different color. Similarly, a printed report may contain additional information such as location of the voids, size of the voids, etc. for later analytical analysis, including recurring similar defects in the part.

Step 72 then proceeds to step 77 which determines if all of the parts have been analyzed. If not, step 77 proceeds to step 79 which increments for the next part number and then returns to step 70 where the above procedure is repeated. When all of the parts have been properly analyzed and the data reported to the user, step 77 instead proceeds to step 81 which terminates the program.

A primary advantage of the program illustrated in FIG. 4 is that it is unnecessary to know precisely the position of the container on the table support prior to performing the CT scan. Instead, since the program illustrated in FIG. 4 identifies the container partitions from the data itself, and then corrects that data to eliminate those partitions, the orientation of the container on the part support is noncritical.

Figure 5:
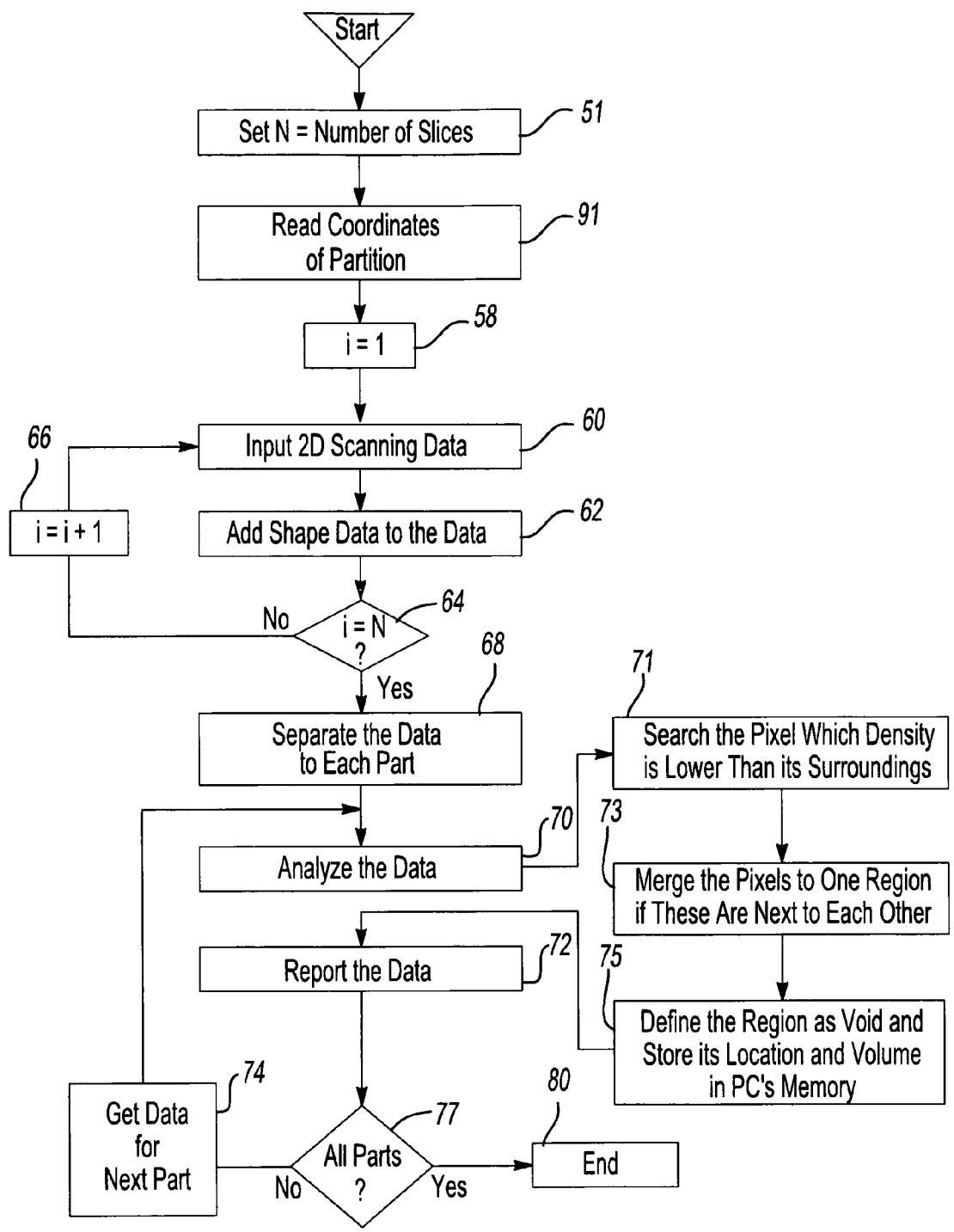
FIG. 5 is a view similar to FIG. 4 but illustrating a modification thereof.

With reference now to FIG. 5, in some instances the coordinates as well as position of the separator or partitions 52 is known in advance. As such, it is unnecessary to analyze the data during the CT scan in order to identify the shape data corresponding to the container partitions 52. Instead, the shape data for the container partitions 52 is predetermined.

Preferably, a physical positioning mechanism, such as a peg, may be used to position the container 50 on the part support 30 so that the position of the partitions 52 is established at the beginning of the CT scan. Alternatively, a metal or magnetic marker 99 (FIG. 2) on the container 30 may be sensed to determine the position of the partitions 52 at the beginning of the CT scan.

In this instance, step 91 in FIG. 5 replaces steps 53, 55 and 56 of FIG. 4. At step 91, the shape data corresponding to the container partitions are read from memory and the data is then processed to detect voids or other flaws in the part. In all other respects, FIG. 5 is identical to FIG. 4 so that a further description thereof is unnecessary.

A primary advantage of the program of FIG. 5 in which the shape data corresponding to the container partitions is predetermined is that processing time necessary to identify and determine the shape data for the container and its partitions is eliminated.

Furthermore, although the container 50 is illustrated as having a fixed number of horizontally separated parts, it will be understood that containers may be stacked upon each other and/or the containers may have horizontal partitions and multiple layers of parts.

In some circumstances, only a portion of the part needs to be scanned in order to determine whether or not the part is defective or not. For example, if the part comprises an engine block, a void very close to the individual combustion chamber or chambers would constitute an unacceptable defect. Conversely, a void in other parts of the engine block would not adversely affect the operation of the engine block when installed in a vehicle. Consequently, a further aspect of the present invention is to only process or analyze data corresponding to the critical areas of the part under examination and to disregard the remainder of the data.

If only a portion of the data for the part is processed, i.e., the data corresponding to the critical areas of the part, the orientation of the part in the container should be determined prior to the CT scan. This can be accomplished physically, i.e. by a fixture in the container for each part, or otherwise such as by attaching a marker to the part or by digitally imaging the part and then analyzing the digital image to determine part orientation prior to the CT scan.

With reference then to FIG. 6, a flowchart is illustrated in which only the data for the critical areas of the part under examination are processed or analyzed by the computer system. At step 80, the variable N is set to the number of 2D data scans previously performed and step 80 then branches to step 82 where the scan data from the radiation detectors 24 is inputted by the computer 40. Step 82 then branches to step 84.

At step 84 the computer 40 reads the predetermined shape of the area of interest from memory. This shape, which corresponds to the area of interest for the CT scan, is predetermined and stored in computer memory. Step 84 then branches to step 86 which sets the variable i to 1 and then proceeds to step 88.

At step 88, the program first determines if i is less than or equal to N and thus determines if all of the desired slices of the part have been processed by the computer 40. If not, step 88 branches to step 90 which determines by comparison with the shape of the area of interest determined at step 84 whether or not the particular slice of the CT scan is of interest for the particular part. If not, step 90 branches to step 92 which increments i and then branches back to step 88. Conversely, if the particular slice obtained during the CT scan contains an area of interest, step 90 instead proceeds to step 94 where the data is stored in a new data set in memory by the computer. Step 94 then proceeds to step 92 and the above process is repeated.

After all of the slices of the CT scan have either been stored in the new data set at step 94 or disregarded, step 88 branches to step 96 where the computer system 40 analyzes the stored data in the new data set in the same fashion as steps 71, 73 and 75 in FIG. 4. Step 96 then proceeds to step 98 where the data is reported through the display device 42.

Consequently, as can be seen by the flowchart of FIG. 6, only the areas of interest and the particular slices of the CT scan corresponding to those areas of interest are stored in the new data set computer memory and processed at step 96 while the remainder of the data is disregarded. This, in turn, minimizes the amount of data necessary for the computer to process at step 96 thus minimizing the amount of time required for the analysis of the CT scan. Furthermore, the method of processing data which only pertains to areas of interest as shown in FIG. 6 may be utilized to analyze a single part or simultaneously analyze multiple parts.

Alternatively, the parts may be oriented such that only the areas of interest are scanned. In this case, step 90 would be eliminated.

With reference now to FIGS. 7 and 8, a still further embodiment of the present invention is shown and which is particularly useful for examining small parts or small portions of a larger part. The CT scanning apparatus 150 includes a robotic arm 152 which is movable about at least one, and preferably several, axes of movement. In the conventional fashion, the robotic arm 152 includes a base 154 and a robotic head 156. The robotic head 156 is preferably movable about an axis of rotation 158.

A CT scanning assembly 160 is mounted to the robotic arm head 156 and is rotatable about the axis 158. The assembly 160 includes both a radiation source 162, such as an x-ray source, as well as a radiation detector 164 at a position spaced from the radiation source 162. In the conventional fashion, the radiation detector 164 provides an output signal which varies as a function of the intensity of radiation received from the radiation source 162. Furthermore, the output from the radiation detector 164 is electrically coupled to a computer system 166 having a display device 168 which both analyzes and displays the data from the radiation detector 164 in the fashion previously described.

With reference now particularly to FIG. 7, a part 170 on a table 171 is shown having one or more risers 172 for which examination is desired. In order to utilize the scanning apparatus 150 shown in FIG. 7, the robotic arm 152 is manipulated so that the riser 172 is positioned within the interior of the scanning assembly 160. The robot 152 is then actuated to rotate the assembly 160 about the axis 158 and, in doing so, collect data relating to the structural integrity of the riser 172.

If multiple data slices of the riser 172 are desired, the robotic arm 152 is programmed to displace its head 156 together with its attached scanner assembly 160 a predetermined distance along the axis 158 following each revolution of the scanning assembly 160. In this fashion, any desired number of data slices for the riser 172 may be obtained.

From the foregoing, it can be seen that the present invention provides an improved CT scanning apparatus and method which achieves many advantages over the previously known devices. In particular, the method of the present invention may be used to scan multiple parts simultaneously. In addition, the processing time required to complete the CT scan, either on multiple parts or on a single part, is reduced by either limiting the data analysis to particular areas of interest in the part or, alternatively, by automatically modifying the data to eliminate data pertaining to partitions of the container.

Having described our invention, however, many modifications thereto will become apparent to those skilled in the art to which it pertains without deviation from the spirit of the invention as defined by the scope of the appended claims.

We claim:

1. System for performing computed tomography to detect an internal structure of a plurality of substantially identical parts comprising:

a radiation source;

at least one radiation detector spaced from said radiation source, said at least one detector generating an output signal representative of the strength of received radiation from the radiation source;

a table which supports the plurality of substantially identical parts positioned between said radiation source and said at least one detector;

at least one of said table and said radiation source being movable relative to the other; and a processor which receives said output signal from said at least one detector as an input signal and, under program control, generates an output representative of at least a portion of the internal structure of parts supported on the table;

wherein said table comprises a container having an interior into which parts are placed.

2. The invention as defined in claim 1 wherein said table comprises a rotary table, said table being positioned on said rotary table, and an actuator which rotates said table about a predetermined axis.

3. The invention as defined in claim 2 wherein said axis is substantially perpendicular to a vector between said radiation source and said detectors.

4. The invention as defined in claim 1 and comprising a marker attached to said container at a predetermined position relative to parts contained in the container.

5. The invention as defined in claim 4 wherein said container contains a plurality of partitions which divide the interior of the container into a plurality of parts containing compartments.

6. The invention as defined in claim 1 and comprising a plurality of radiation detectors, wherein said radiation detectors are arranged in an arc centered about said radiation source.

7. The invention as defined in claim 6 wherein said radiation detectors are arrayed in a two-dimensional array.

8. The invention as defined in claim 1 wherein the parts are constructed at least partially of metal.

9. The invention as defined in claim 1 wherein said computer system is programmed to reconstruct an image of the internal structure of only a portion of each workpiece.

10. System for performing computed tomography to detect an internal structure of a plurality of substantially identical parts comprising:

a radiation source;

at least one radiation detector spaced from said radiation source, said at least one detector generating an output signal representative of the strength of received radiation from the radiation source;

a table which supports the plurality of substantially identical parts positioned between said radiation source and said at least one detector;

at least one of said table and said radiation source being movable relative to the other; and a processor which receives said output signal from said at least one detector as an input signal and, under program control, generates an output representative of at least a portion of the internal structure of parts supported on the table;

wherein said table comprises a rotary table, said table being positioned on said rotary table, and an actuator which rotates said table about a predetermined axis;

wherein said axis is substantially perpendicular to a vector between said radiation source and said detectors;

a second actuator which moves the table a predetermined increment in the direction of said table axis per revolution of said table.

11. The invention as defined in claim 10 wherein said computer system is programmed to reconstruct an image of the internal structure of only a portion of each workpiece.

12. System for performing computed tomography to detect an internal structure of a plurality of substantially identical parts comprising:

a radiation source;

at least one radiation detector spaced from said radiation source, said at least one detector generating an output signal representative of the strength of received radiation from the radiation source;

a table which supports the plurality of substantially identical parts positioned between said radiation source and said at least one detector;

at least one of said table and said radiation source being movable relative to the other; and a processor which receives said output signal from said at least one detector as an input signal and, under program control, generates an output representative of at least a portion of the internal structure of parts supported on the table;

wherein said computer system is programmed to disregard output signals from said detectors corresponding to said table.

13. The invention as defined in claim 12 wherein said computer system is programmed to reconstruct an image of the internal structure of only a portion of each workpiece.

14. The invention as defined in claim 12 wherein the part is constructed at least partially of metal.

15. A method for performing computed tomography on a plurality of substantially identical parts to detect an internal structure of the parts using a rotating table positioned between a radiation source and a plurality of radiation detectors, said plurality of detectors producing an output signal representative of the strength of the radiation received by the detectors, comprising the steps of:

collecting data for the radiation detectors responsive to the plurality of substantially identical parts during revolution of the table for each revolution of the table; and reconstructing from the collected data an output representative of at least a portion of the internal structure of at least a portion of the parts supported on the table;

wherein said reconstructing step further comprises the steps of identifying adjacent areas corresponding to voids and merging said identified adjacent areas together.

16. The method as defined in claim 15 wherein said parts are contained in a container having partitions, and wherein said disregarding step comprises the step of disregarding data corresponding to the partitions.

17. The method as defined in claim 15 wherein the part is constructed at least partially of metal.

18. A method for performing computed tomography on a plurality of substantially identical parts to detect an internal structure of the parts using a rotating table positioned between a radiation source and a plurality of radiation detectors, said plurality of detectors producing an output signal representative of the strength of the radiation received by the detectors, comprising the steps of:

collecting data for the radiation detectors responsive to the plurality of substantially identical parts during revolution of the table for each revolution of the table; and reconstructing from the collected data an output representative of at least a portion of the internal structure of at least a portion of the parts supported on the table;

wherein the axis of the table is substantially perpendicular to a vector between the radiation source and the at least one radiation detectors, and further comprising the step of moving the table a predetermined increment along the axis per revolution of the table.

19. The method as defined in claim 18 wherein said parts are contained in a container having partitions, and wherein said disregarding step comprises the step of disregarding data corresponding to the partitions.

20. The method as defined in claim 18 wherein the part is constructed at least partially of metal.

21. A method for performing computed tomography on a plurality of substantially identical parts to detect an internal structure of the parts using a rotating table positioned between a radiation source and a plurality of radiation detectors, said plurality of detectors producing an output signal representative of the strength of the radiation received by the detectors, comprising the steps of:
  collecting data for the radiation detectors responsive to the plurality of substantially identical parts during revolution of the table for each revolution of the table;
  reconstructing from the collected data an output representative of at least a portion of the internal structure of at least a portion of the parts supported on the table; and
  disregarding data from the detector for portions of the part other than said at least one portion of the part.

22. The method as defined in claim 21 wherein said parts are contained in a container having partitions, and wherein said disregarding step comprises the step of disregarding data corresponding to the partitions.

23. The method as defined in claim 21 and comprising the steps of gathering data representative of the structure of an empty table from the detectors during at least one revolution of the table, and wherein said reconstructing step comprises the step of subtracting said gathered table data from said collected data.

24. The method as defined in claim 21 wherein the part is constructed at least partially of metal.

25. A method for performing computed tomography on a plurality of substantially identical parts to detect an internal structure of the parts using a rotating table positioned between a radiation source and a plurality of radiation detectors, said plurality of detectors producing an output signal representative of the strength of the radiation received by the detectors, comprising the steps of:
  collecting data from the at least one radiation detector during revolution of the table for each revolution of the table only for a predetermined portion of the part; and
  reconstructing from the collected data an output representative of the internal structure of the predetermined portion of the part mounted on the table;
  wherein said at least one part is mounted in a container having partitions, and further comprising the steps of:
  modifying the collected data to eliminate data corresponding to partitions; and
  reconstructing from the modified collected data an image of the internal structure of the parts in the container.

26. The method as defined in claim 25 wherein said reconstructing step further comprises the step of forming an image representative of the internal structure of the part.

27. The method as defined in claim 26 wherein said image forming step includes the step of using different colors in the image for different part densities.

28. System for performing computed tomography comprising:
  a radiation source;
  at least one radiation detector spaced from said radiation source, said at least one detector generating an output signal representative of the strength of received radiation from the radiation source;
  a table which supports a plurality of parts positioned between said radiation source and said at least one detector;
  said table being movable relative to said radiation source and said at least one detector;
  a processor which receives said output signal from said at least one detector as an input signal and, under program control, generates an output representative of at least a portion of the internal structure of parts supported on the table;
  a marker attached to said container at a predetermined position relative to parts contained in the container; and
  wherein said container contains a plurality of partitions which divide the interior of the container into a plurality of parts containing compartments.

29. The invention as defined in claim 28 and comprising a plurality of radiation detectors, wherein said radiation detectors are arranged in an arc centered about said radiation source.

30. A method for performing computed tomography on a plurality of parts using a rotating table positioned between a radiation source and a plurality of radiation detectors, said plurality of detectors producing an output signal representative of the strength of the radiation received by the detectors, comprising the steps of:
  collecting data for the radiation detectors responsive to the plurality of parts during revolution of the table for each revolution of the table;
  reconstructing from the collected data an output representative of at least a portion of the internal structure of at least a portion of the parts supported on the table; and
  disregarding data from the detector for portions of the part other than said at least one portion of the part;
  wherein said parts are contained in a container having partitions, and wherein said disregarding step comprises the step of disregarding data corresponding to the partitions.

31. The method as defined in claim 30 and comprising the steps of gathering data representative of the structure of an empty table from the detectors during at least one revolution of the table, and wherein said reconstructing step comprises the step of subtracting said gathered table data from said collected data.

32. A method for performing computed tomography on parts mounted in a container having partitions using a rotating table positioned between a radiation source and a plurality of radiation detectors, said plurality of detectors producing an output signal representative of the strength of the radiation received by the detectors, comprising the steps of:
  collecting data from the at least one radiation detector during revolution of the table for each revolution of the table only for a predetermined portion of the part;
  modifying the collected data to eliminate data corresponding to partitions; and
  reconstructing from the modified collected data an image of the internal structure of the parts in the container.

33. The method as defined in claim 30 wherein said reconstructing step further comprises the step of forming an image representative of the internal structure of the part.

* * * * *